United States Patent

Karcher

[11] Patent Number: 5,558,754
[45] Date of Patent: Sep. 24, 1996

[54] METHOD FOR PREPARING 3-ALKYL-2,6-DICHLOROACYLANILIDES BY ELECTROLYTIC DEBROMINATION OF 3-ALKYL-4-BROMO-2,6-DICHLOROA CYLANILIDES

[75] Inventor: Thomas Karcher, Hofheim, Germany

[73] Assignee: Hoechst Aktiengesllschaft, Germany

[21] Appl. No.: 346,031

[22] Filed: Nov. 29, 1994

[30] Foreign Application Priority Data

Dec. 1, 1993 [DE] Germany ............... 43 40 896.6

[51] Int. Cl.⁶ .................................................. C25B 3/00
[52] U.S. Cl. ........................ 205/431; 205/436; 205/456
[58] Field of Search ........................ 204/59 R, 72, 204/73 R

[56] References Cited

U.S. PATENT DOCUMENTS 3,928,432  12/1975  Becher et al. .................. 204/59 R
5,068,392  11/1991  McKendry et al. ................ 560/46

FOREIGN PATENT DOCUMENTS 0593251  4/1994  European Pat. Off. .
2331711  1/1975  Germany .

*Primary Examiner*—Kathryn Gorgos
*Assistant Examiner*—Edna Wong
*Attorney, Agent, or Firm*—Connolly & Hutz

[57] ABSTRACT

A method for preparing 3-alkyl-2,6-dichloroacylanilides by electrolytic debromination of 3-alkyl-4-bromo-2,6-dichloroacylanilides.

A method for preparing a 3-alkyl-2,6-dichloroacylanilide of the formula I

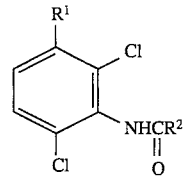

in which $R^1$, $R^2$ are, independently of one another, $(C_1-C_4)$-alkyl, by bromoalkylacylanilides of the formula II

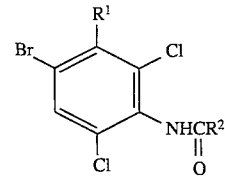

in which $R^1$, $R^2$ have the above-specified meaning, being electrolytically debrominated.

23 Claims, No Drawings

METHOD FOR PREPARING 3-ALKYL-2,6-DICHLOROACYLANILIDES BY ELECTROLYTIC DEBROMINATION OF 3-ALKYL-4-BROMO-2,6-DICHLOROACYLANILIDES

The invention describes a method for preparing 3-alkyl-2,6-dichloroacylanilides by electrolytic debromination of 3-alkyl-4-bromo-2,6-dichloroacylanilides.

Alkylacylanilides are valuable intermediates for the preparation of physiologically active compounds (U.S. Pat. No. 5,006,656, U.S. Pat. No. 4,937,350).

3-alkyl-2,6-dichloroacylanilides are not accessible by direct chlorination of 3-alkylacylanilides, since in the process the corresponding 4-chloro-substituted product is also formed at the same time. On the other hand, 3-alkyl-4-bromo-2,6-dichloroacylanilide can be obtained in high yield by bromination and subsequent chlorination.

Reductive dehalogenations on aromatic rings are described in the literature. These require toxic reagents such as triphenyltin hydride (J. Org. Chem. 1963, 28, 2332) or expensive reagents such as, e.g. lithium aluminum hydride (J. Chem. Res. 1990, 190), which makes these methods unsuitable for industrial purposes. The catalytic dehalogenation by means of hydrogen proceeds with low selectivity.

There was therefore a great need for a method which makes 3-alkyl-2,6-dichloroacylanilides accessible in high yield and purity.

This object is achieved by a method for preparing a 3-alkyl-2,6-dichloroacylanilide of the formula I

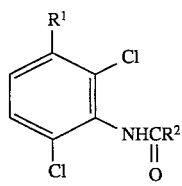

in which $R^1$, $R^2$ are, independently of one another, $(C_1-C_4)$-alkyl, which comprises bromoalkylacylanilides of the formula II

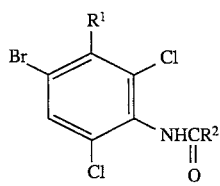

in which $R^1$, $R^2$ have the above-specified meaning, being electrolytically debrominated.

The method is particularly important for the compounds of formula I in which $R^1$ and $R^2$ are both methyl.

The reaction apparatus used for the electrolysis is an appliance which can be divided, by a diaphragm or a membrane, into an anode compartment and a cathode compartment, the debromination taking place at the cathode. The electrolysis is carried out at room temperature or slightly elevated temperature.

In many cases it has proved useful to employ, as the reaction medium on the anode side, an aqueous solution of an acid or an alkali metal halide having adequate conductivity. The anode material is selected in such a way that it is inert under reaction conditions. If an aqueous acid such as, e.g. sulphuric acid is used as the anolyte, a dimensionally stable anode or a platinum anode is preferably employed. If an aqueous alkali metal bromide solution is used as the anolyte, it has proved useful to employ an anode based on carbon, such as, e.g., graphite.

On the cathode side, lower alcohols are used as the solvent. Preferably, methanol is employed. The cathode material used is an electrically conductive material which has adequate stability with respect to halide-containing solutions and is distinguished by a hydrogen overpotential which is sufficiently high for the debromination of the compounds I. Preferably carbon-based materials are used such as, e.g., graphite.

To increase the hydrogen overpotential, the catholyte can be admixed with catalytic amounts of a salt of the following elements: Cu, Ag, Au, Zn, Cd, Hg, Sn, Pb, Ti, Zr, Bi, V, Ta, Cr, Ce, Co, Ni. If salts are employed to increase the hydrogen overpotential, they are preferably salts of the elements Pb, Sn, Bi, Zn, Cd, Cr. In particular, Pb salts are employed as a catholyte additive. The preferred anions of the said salts are chloride, sulfate, nitrate or acetate. The salts can be admixed to the electrolyte directly or alternatively, prepared in the solution by the addition of oxides or carbonates. The salt concentration of the electrolyte is expediently from $10^{-6}$ to 10% by weight, preferably from $10^{-5}$ to $10^{-1}$% by weight, especially from $10^{-4}$ to $4\times10^{-2}$% by weight, in each case based on the total amount of the electrolysis solution.

The conductivity of the electrolyte in the cathode compartment is provided by a supporting electrolyte which is inert under the reaction conditions and which is proportioned in such a way that adequate conductivity is achieved. For example, a carboxylic acid salt which is soluble in the electrolyte, such as sodium acetate, can be employed for this purpose.

The advantage of the invention compared to other methods for debromination consists in the highly selective removal of the bromine atom from the molecule, without adversely affecting other functional groups.

Monitoring of the reaction can be effected by common analytical methods such as, e.g., gas chromatography. The conversion can also be calculated from the electric charge transferred and the amount of hydrogen formed on the cathode, since reactions other than the debromination of the compounds I and generation of hydrogen are not observed. In particular, the chlorine atoms in compounds of the type I are not eliminated reductively if the electric charge required for complete debromination is exceeded.

The synthesis of the starting compounds can be carried out in a simple manner by methods known in the literature, starting from alkylanilines. For example, the 4-bromo-2,6-dichloro-3-methylacetanilide employed in the following examples can be obtained by reacting m-toluidine with acetic anhydride. The 3-methylacetanilide thus obtained is then reacted with bromine, which leads to selective bromination in the 4-position. The subsequent reaction with an excess of chlorine gives the 4-bromo-2,6-dichloro-3methylacetanilide in good yield and with good selectivity.

EXAMPLE 1

Starting material: 23.1 g of 4-bromo-2,6-dichloro-3-methylacetanilide
Catholyte: 300 ml of methanol, 6.83 g of sodium acetate, 30°–35° C.
Anolyte: 300 ml of 10% strength sulphuric acid, 30°–35° C.
Cell: divided flow cell, platinum anode (14 cm$^2$), graphite cathode (14 cm$^2$), Nafion 417 membrane
Current: 1400 mA
Electric charge: 4.17 Ah
Conversion: 71%

EXAMPLE 2

Starting material: 23.1 g of 4-bromo-2,6-dichloro-3-methylacetanilide

Catholyte: 300 ml of methanol, 6.83 g of sodium acetate, 200 mg of lead(II) acetate trihydrate, 30°–35° C.
Anolyte: 300 ml of 10% strength sulphuric acid, 30°–35° C.
Cell: divided flow cell, platinum anode (14 cm$^2$), graphite cathode (14 cm$^2$), Nafion 417 membrane
Current: 1400 mA
Electric charge: 4.17 Ah
Conversion: 79%

EXAMPLE 3

Starting material: 23.1 g of 4-bromo-2,6-dichloro-3-methylacetanilide
Catholyte: 300 ml of methanol, 6.83 g of sodium acetate, 30°–35° C. 200 mg of lead(II) acetate tihydrate, 30°–35° C.
Anolyte: 300 ml of 30% strength sodium bromide solution, 30°–35° C.
Cell: divided flow cell, graphite anode (14 cm$^2$), graphite cathode (14 cm$^2$), Nafion 417 membrane
Current: 1400 mA
Electric charge: 5.63 Ah
Conversion: quantitative
Work-up: The pH of the catholyte is set to 4 by means of dilute sulphuric acid. The solution is concentrated on a rotary evaporator to about half of its original volume and the reaction product is isolated by filtration. 14.3 g of 2,6-dichloro-3-methylacetanilide are obtained.

I claim:

1. A method of preparing a 3-alkyl-2,6-dichloroacylanilide of the formula I

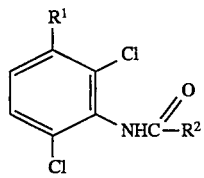

in which $R^1$ and $R^2$ are, independent of one another, $C_1$–$C_4$-alkyl, comprising electrolytically debrominating a bromo-alkylacylanilide of the formula II

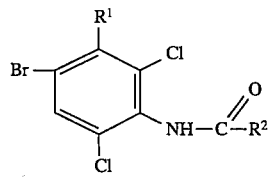

in which $R^1$ and $R^2$ are as defined above in a reaction apparatus for electrolysis which is divided into an anode compartment containing an anolyte and a cathode compartment containing a catholyte, wherein the anolyte is an acid or alkali metal halide in aqueous solution having adequate conductivity and the catholyte contains a alcohol as a solvent and a electrolyte to provide conductivity.

2. The method as claimed in claim 1, wherein the progress of the debromination is determined by monitoring amounts of bromine removal or hydrogen production.

3. The method as claimed in claim 1, wherein $R^1$ and $R^2$ are $C_1$–$C_2$-alkyl.

4. The method as claimed in claim 1, wherein $R^1$ and $R^2$ are methyl.

5. The method as claimed in claim 1, wherein said electrolytically debrominating step is carried out in an apparatus comprising:
an anode compartment containing an anode and a reaction medium and
a cathode compartment containing a cathode and a reaction medium,
said anode compartment being separated by a membrane or a diaphragm from said cathode compartment.

6. The method as claimed in claim 5, wherein said electrolytically debrominating step is carried out at the cathode of said cathode compartment.

7. The method as claimed in claim 5, wherein an anode in said anode compartment contains a material which is inert under reaction conditions employed in said anode compartment.

8. The method as claimed in claim 5, wherein the catholyte is a $C_1$–$C_2$-alkanol.

9. The method as claimed in claim 8, wherein said $C_1$–$C_2$-alkanol is methanol.

10. The method as claimed in claim 5, wherein the cathode of said cathode compartment contains an electrically conductive material which is stable with respect to halide-containing solutions and said electrically conductive material has a hydrogen overpotential sufficiently high for electrolytically debrominating a bromoalkylacylanilide.

11. The method as claimed in claim 10, wherein the electrically conductive material contains carbon.

12. The method as claimed in claim 11, wherein the electrically conductive material contains graphite.

13. The method as claimed in claim 5, wherein the catholyte is admixed with a catalytic amount of a hydrogen-overpotential-increasing salt.

14. The method as claimed in claim 13, wherein the salt is a salt of Cu, Ag, Au, Zn, Cd, Hg, Sn, Pb, Ti, Zr, Bi, V, Ta, Cr, Ce, Co, or Ni.

15. The method as claimed in claim 13, wherein the salt is a salt of Pb, Sn, Bi, Zn, Cd, or Cr.

16. The method as claimed in claim 13, wherein the salt is a salt of Pb.

17. The method of claim 13, wherein the salt is a chloride, sulphate, nitrate or acetate.

18. The method as claimed in claim 13, wherein the salt is present in a concentration from $10^{-6}$ to 10% by weight.

19. The method as claimed in claim 13, wherein the salt is present in a concentration from $10^{-5}$ to $10^{-1}$% by weight.

20. The method as claimed in claim 13 wherein the salt is present in said reaction medium in a concentration from $10^{-4}$ to $4 \times 10^{-2}$% by weight.

21. The method as claimed in claim 5, wherein the cathode compartment contains a supporting electrolyte which is inert under reaction conditions employed in said cathode compartment.

22. The method as claimed in claim 21, wherein the supporting electrolyte is a salt of a carboxylic acid.

23. The method as claimed in claim 21, wherein the supporting electrolyte is sodium acetate.

* * * * *